US006734387B2

(12) United States Patent
Kafka et al.

(10) Patent No.: US 6,734,387 B2
(45) Date of Patent: May 11, 2004

(54) METHOD AND APPARATUS FOR MICRO-MACHINING OF ARTICLES THAT INCLUDE POLYMERIC MATERIALS

(75) Inventors: James D. Kafka, Palo Alto, CA (US); Mingwei Li, Sunnyvale, CA (US)

(73) Assignee: Spectra Physics Lasers, Inc., Mountain View, CA (US)

( * ) Notice: Subject to any disclaimer, the term of this patent is extended or adjusted under 35 U.S.C. 154(b) by 0 days.

(21) Appl. No.: 10/114,337

(22) Filed: Apr. 1, 2002

(65) Prior Publication Data

US 2002/0185478 A1 Dec. 12, 2002

Related U.S. Application Data

(63) Continuation-in-part of application No. 09/321,499, filed on May 27, 1999, now Pat. No. 6,373,565.

(51) Int. Cl.[7] .......... B23K 26/38

(52) U.S. Cl. .......... 219/121.68; 219/121.69; 264/400

(58) Field of Search .......... 219/121.68, 121.69; 372/18; 264/400

(56) References Cited

U.S. PATENT DOCUMENTS

| | | | | |
|---|---|---|---|---|
| 3,626,143 A | | 12/1971 | Fry | 219/121.69 |
| 4,377,340 A | | 3/1983 | Green et al. | 356/237 |
| 4,630,276 A | | 12/1986 | Moran | 372/15 |
| 4,933,944 A | * | 6/1990 | McGraw | 372/18 |
| 4,942,582 A | | 7/1990 | Kintz et al. | 372/18 |
| 4,989,984 A | | 2/1991 | Salinger | 356/445 |
| 5,127,726 A | | 7/1992 | Moran | 356/237 |
| 5,170,063 A | | 12/1992 | Miyazaki et al. | 250/572 |
| 5,177,559 A | | 1/1993 | Batchelder | 356/237 |
| 5,361,275 A | * | 11/1994 | Opower | |
| 5,394,413 A | | 2/1995 | Zayhowski | 372/10 |
| 5,410,559 A | * | 4/1995 | Nighan, Jr. et al. | |
| 5,623,341 A | | 4/1997 | Hunt | 356/300 |
| 5,627,854 A | | 5/1997 | Knox | 372/99 |
| 5,699,160 A | * | 12/1997 | Barenboim et al. | |
| 5,712,701 A | | 1/1998 | Clementi et al. | 356/237.1 |
| 5,812,308 A | | 9/1998 | Kafka et al. | 359/346 |
| 5,834,160 A | | 11/1998 | Ferry et al. | 430/313 |
| 5,936,983 A | | 8/1999 | Yusong et al. | 372/22 |
| 5,940,418 A | * | 8/1999 | Shields | |
| 5,987,049 A | * | 11/1999 | Weingarten et al. | 372/18 |
| 6,061,370 A | | 5/2000 | Yin | 372/22 |
| 6,071,677 A | * | 6/2000 | Ishimatsu et al. | |
| 6,113,835 A | * | 9/2000 | Kato et al. | 219/121.69 |
| 6,157,663 A | | 12/2000 | Wu et al. | 372/75 |
| 6,185,235 B1 | | 2/2001 | Cheng et al. | 372/39 |
| 6,188,704 B1 | * | 2/2001 | Kwon et al. | |
| 6,246,706 B1 | | 6/2001 | Kafka et al. | 372/24 |
| 6,552,301 B2 | * | 4/2003 | Herman et al. | 219/121.68 |
| 2002/0003130 A1 | | 1/2002 | Sun | 219/121.68 |

FOREIGN PATENT DOCUMENTS

| | | | |
|---|---|---|---|
| DE | 195 29 656 A1 | 2/1997 | G03F/7/20 |
| EP | 0 818 858 A2 | 1/1998 | H01S/3/0941 |
| WO | WO 98/33096 | 7/1998 | G03F/1/08 |

* cited by examiner

*Primary Examiner*—Geoffrey S Evans
(74) *Attorney, Agent, or Firm*—Paul Davis; Heller Ehrman White & McAuliffe

(57) ABSTRACT

A micro-machining apparatus includes a mode-locked, infrared laser system with a high reflector and an output coupler that define an oscillator cavity which produces an output beam. A gain medium and a mode locking device are positioned in the oscillator cavity. A diode pump source produces a pump beam that is incident on the gain medium. A second harmonic generator is coupled to the oscillator cavity. A third harmonic generator is coupled to the second harmonic generator and produces a UV output beam. An output beam directing apparatus directs the output beam to a polymeric surface of an article. At least a portion of the polymeric material is micro-machined by the output beam.

40 Claims, 1 Drawing Sheet

METHOD AND APPARATUS FOR MICRO-MACHINING OF ARTICLES THAT INCLUDE POLYMERIC MATERIALS

CROSS REFERENCE TO RELATED APPLICATIONS

This application is a continuation-in-part of U.S. Ser. No. 09/321,499 filed May 27, 1999, now U.S Pat. No. 6,373, 565 which is related to U.S. Pat. No. 6,246,706 and to U.S. Ser. No. 09/322,121 filed. May 27, 1999, now U.S. Pat. No. 6,421,573 which applications are incorporated herein by reference.

BACKGROUND OF THE INVENTION

1. Field of the Invention

This invention relates generally to diode-pumped solid state UV laser systems, and their methods of use, and more particularly to diode-pumped solid state UV laser systems that are used in micro-machining of polymeric articles.

2. Description of Related Art

The increasing demand for electronic devices is driving the need for laser materials processing in microelectronics industry. Among a wide variety of laser applications, micro-machining of polymers using diode-pumped solid-sate (DPSS) UV lasers is gaining more and more attention. Due to the short wavelengths (355 nm or 266 nm) of UV lasers, small feature size and minimum thermal damage, both the desired features of miniaturized devices, can be obtained.

However, compared with the processes using lasers of longer wavelength such as $CO_2$ lasers, those using UV lasers are generally slower. So there is a constant effort to increase the processing speed and thus increase the throughput of production processes involving UV lasers.

Most DPSS UV lasers currently used in electronics industry are Q-switched lasers with pulsewidths ranging from 5 ns to 100 ns and pulse repetition rates ranging from 1 kHz to 100 kHz. A 355 nm mode locked laser at 8 MHz repetition rate produces an average power of 4 W at output, with a repetition rate of 80 MHz and a pulsewidth of 10 ps. It is expected that the mode-locked laser can provide certain unique advantages in laser micro-machining of certain materials due to its ultrafast pulse and high repetition rate.

There is a need for a diode-pumped solid-state laser that can cut or scribe polymer materials at an increased speed.

SUMMARY OF THE INVENTION

Accordingly, an object of the invention is to provide an improved micro-machining apparatus, and its method of use.

Another object of the present invention is to provide a diode-pumped solid state laser, and its method of use, that can cut or scribe polymer materials at increased speeds.

These and other objects of the present invention are achieved in a micro-machining apparatus. The apparatus includes a mode-locked, infrared laser system with a high reflector and an output coupler that define an oscillator cavity which produces an output beam. A gain medium and a mode locking device are positioned in the oscillator cavity. A diode pump source produces a pump beam that is incident on the gain medium. A second harmonic generator is coupled to the oscillator cavity. A third harmonic generator is coupled to the second harmonic generator and produces a UV output beam. An output beam directing apparatus directs the output beam to a polymeric surface of an article. At least a portion of the polymeric material is micro-machined by the output beam.

In another embodiment of the present invention, a micro-machining apparatus includes a mode-locked, infrared laser system with a high reflector and an output coupler that define an oscillator cavity. The oscillator cavity produces an output beam. A gain medium and a mode locking device are positioned in the oscillator cavity. A diode pump source produces a pump beam that is incident on the gain medium and a first amplifier. A second harmonic generator is coupled to the oscillator cavity. A third harmonic generator is coupled to the second harmonic generator and produces a UV output beam. An output beam directing apparatus directs the output beam to a polymeric surface of an article. At least a portion of the polymeric material is micro-machined by the output beam.

In another embodiment of the present invention, a method of micro-machining a polymeric surface of an article provides a mode-locked, infrared laser system that includes a high reflector and an output coupler which define an oscillator cavity. A gain medium and a mode locking device are positioned in the oscillator cavity. A UV output beam is produced from the laser system. The UV output beam is then used to micro-machine at least a portion of the polymeric surface of the article.

DETAILED DESCRIPTION

The present invention provides a micro-machining apparatus that includes a laser system. In one embodiment, the laser system includes an oscillator system or an oscillator/amplifier system. The oscillator/amplifier system is similar to the oscillator system but includes one or more amplifiers. The oscillator and oscillator/amplifier systems can be coupled with second, third, fourth and fifth harmonic generators. A second harmonic generator can be used alone with the oscillator and oscillator/amplifier systems and in various combinations with third, fourth and fifth harmonic generators. Additionally, the harmonic generators can be coupled with an OPO. The OPO can be pumped by a fundamental beam from an oscillator or from the harmonic generators. An output of the OPO can be mixed with the harmonic generators to generate a variable wavelength source.

In one embodiment, the oscillator system includes an Nd:$YVO_4$ gain media and is mode locked by a multiple quantum well absorber. In a specific embodiment of this oscillator system, the oscillator is pumped by a single fiber-coupled diode bar that provides 13 watts of pump power incident on the Nd:$YVO_4$ gain media, and typically produces 5–6 watts of 5–15 picosecond pulses at 80 MHz repetition rate. In another embodiment, an oscillator/amplifier system includes an Nd:$YVO_4$ gain media mode locked by a multiple quantum well absorber, a double pass amplifier and two single pass amplifiers. Each of the amplifiers has an Nd:$YVO_4$ gain media and is pumped by two fiber-coupled diode pump sources. This oscillator/amplifier system produces 25–30 watts of 5–15 picosecond pulses at 80 MHz repetition rate.

The oscillator and oscillator/amplifier systems can be mode locked with a multiple quantum well saturable absorber, a non-linear mirror mode locking method, a polarization coupled mode locking method or other mode locking techniques, including but not limited to use of an AO modulator. An example of a quantum well saturable absorber is disclosed in U.S. Pat. No. 5,627,854, incorporated herein by reference. An example of a non-linear mirror mode locking method is disclosed in U.S. Pat. No. 4,914, 658, incorporated herein by reference. An example of a polarization coupled mode locking method is disclosed U.S. Pat. No. 6,021,140 assigned to the same assignee as this application and incorporated herein by reference. In order to producer shorter pulses and a single output beam the gain media is positioned adjacent to a fold mirror as described in U.S. Pat. No. 5,812,308, incorporated herein by reference.

A high power oscillator system with the performance of an oscillator/amplifier system is achieved by using multiple fiber-coupled diodes and either a non-linear mirror mode locking technique or a polarization coupled mode locking method. This high power oscillator system produces 10–20 watts of output power with 4–10 picosecond pulses at a repetition rate of 80–120 MHz.

Figure 1:
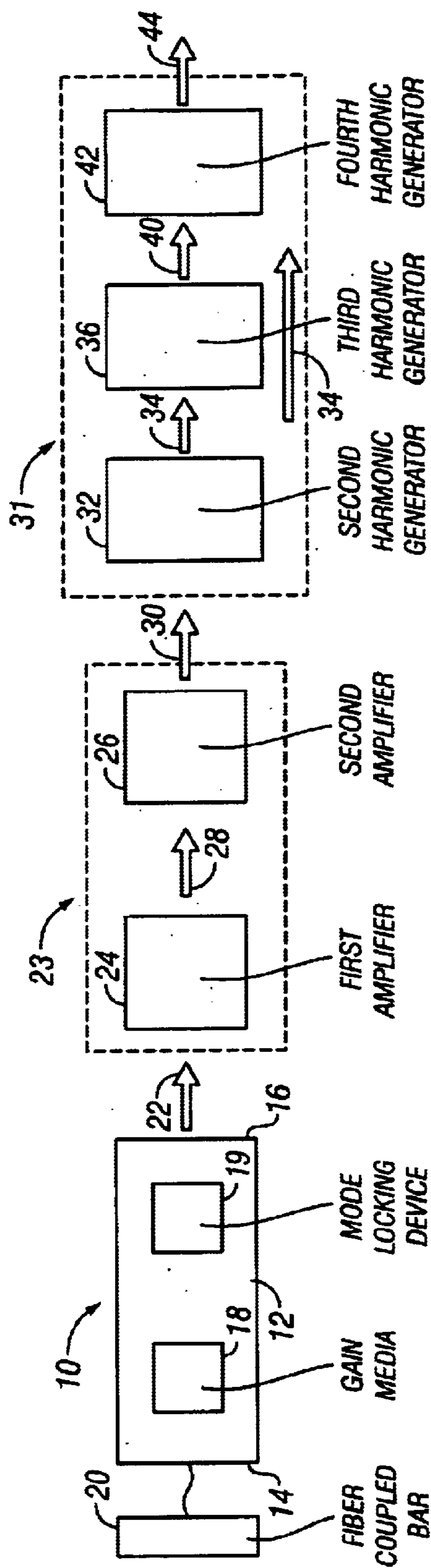
FIG. 1 is a block diagram of a laser, laser/amplifier system useful with the present invention.

High repetition rates are desirable for applications where the laser system is used as a quasi-CW source. For some applications, 80 MHz repetition rate is sufficiency high to be consider to be quasi-CW. This repetition rate is achieved with an oscillator cavity length of 1.8 meters. When the cavity length is shorted to 0.4 meters the repetition rate increases to 350 MHz. Referring now to FIG. 1, one embodiment of an oscillator system 10 has a resonator cavity 12 defined by a high reflector 14 and an output coupler 16. A gain media 18 is positioned in resonator cavity 12. Suitable gain media 18 include but are not limited to, $Nd:YVO_4$, Nd:YAG, Nd:YLF, Nd:Glass, Ti:sapphire, Cr:YAG, Cr:Forsterite, Yb:YAG, Yb:glass, Yb:KGW, Yb:KYW and the like. A preferred gain media 18 is $Nd:YVO_4$. A mode locking device 19 is positioned in oscillator cavity 12. In the embodiment, oscillator system 10 is mode locked and pumped by a fiber-coupled bar 20 that produces 13 watts of power. Oscillator cavity 12 can produce 1 to 6 watts of power nominally at a 80 MHz repetition rate with pulse widths of 5 to 15 picoseconds.

Optionally included is one or more amplifiers, generally denoted as 23. An output beam 22 from resonator cavity 12 can be amplified by a first amplifier 24. A second amplifier 26 can be included. Additional amplifiers may also be included to increase power. Typically, amplifiers 24 and 26 have the same gain media used in resonator cavity 12. $Nd:YVO_4$ is a suitable gain media material because it provides high gain in an amplifier. The higher gain of $Nd:YVO_4$ provides a simplified amplifier design requiring fewer passes through the gain media. Amplifiers 24 and 26 produce output beams 28 and 30 respectively. Amplifiers 24 and 26 can be single pass, double pass and four pass. A four pass amplifier is disclosed in U.S. Pat. No. 5,812,308, assigned to the same assignee as this application and incorporated herein by reference. Oscillator/amplifier system 10 using an oscillator, a double pass amplifier and two single pass amplifiers can provide 30 watts of average power.

Output beams 22, 28 or 30 can be incident on a harmonic generator generally denoted as 31 and can include a second harmonic generator 32. An output 34 from second harmonic generator 32 can be incident on a third harmonic generator 36 to produce an output beam 40. Output 34 can be incident on a fourth harmonic generator 42 to produce an output beam 44. It will be appreciated that oscillator system 10 can include various combinations of harmonic generators 32, 36, 42 as well as a fifth harmonic generator or an OPO. Second harmonic generator 32 can use non-critically phase matched LBO, third harmonic generator 36 can employ type II LBO and fourth harmonic generator 42 can use type I BBO.

In a specific embodiment, oscillator system 10 includes oscillator cavity 12 with harmonic generation. Output beam 22 is incident on second harmonic generator 32. In this specific embodiment, oscillator system 10 may also include third and fourth harmonic generators 36 and 42. The output power of this oscillator system 10 is 5 watts at 1064 nm. A harmonic generation system produces 2 watts at 532 nm or 1 watt at 355 nm or 200 milliwatts at 266 nm.

In another specific embodiment, $Nd:YVO_4$ is the gain media of oscillator/amplifier system 10, and 29 watts of 7 picosecond pulses at 1064 nm is produced. The harmonic generation system can generate 22 watts at 532 nm or 11 watts at 355 nm or 4.7 watts at 266 nm.

In another specific embodiment, oscillator/amplifier system 10 includes oscillator cavity 12, a four pass amplifier 24 and second harmonic generator 32 to produce 2 watts at 532 nm. This oscillator/amplifier system can pump an OPO that utilizes non-critically phase matched LBO as described in Kafka, et al., J. Opt. Soc. Am. B 12, 2147–2157 (1995) incorporated herein by reference.

In another specific embodiment, oscillator/amplifier system 10 includes oscillator cavity 12, a double pass amplifier 24 and three single pass amplifiers 26 that produces 42 watts of 7 picosecond pulses at 1064 nm. This oscillator/amplifier system can pump an OPO using non-critically phase-matched KTA and produce an output beam at 1535 nm. The output beam at 1535 nm can be mixed with a 1064 nm beam to provide 11.6 watts at 629 nm, as described in Nebel, et al., in *Conference on Lasers and Electro-Optics*, Vol. 6 of 1998 OSA Technical Digest Series (Optical Society of America, Washington, D.C., 1998) postdeadline paper CPD3. 40 watts fiber-coupled bars, commercially available from Spectra Physics Semiconductor Lasers, Tucson, Ariz. can be used to increase the output power of oscillator or oscillator/amplifier systems 10. The use of an $Nd:YVO_4$ gain media 18 with a doping level of less than 0.5% can also be used to increase the output power of oscillator or oscillator/amplifier systems 10. The combination of the 40 watt fiber-coupled bars with the low doped $Nd:YVO_4$ gain media greatly increases the output power of oscillator and oscillator/amplifier systems 10. Use of low doped $Nd:YVO_4$ gain media 18 can also reduce the sensitivity of oscillator cavity 12 to misalignment as well as improve the output beam quality from an amplifier 24 or 26. The use of low doped $Nd:YVO_4$ gain media, a longer $Nd:YVO_4$ gain media as well as a larger pump volume in $Nd:YVO_4$ gain media is disclosed in commonly owned U.S. Pat. No. 6,185,235, incorporated herein by reference.

Hereafter, oscillator system and/or oscillator/amplifier system 10, shall collectively be referred to as laser system 110, and output beams 22, 28, 30, 34, 40 or 44 are collectively denoted as output beam 112.

Figure 2:
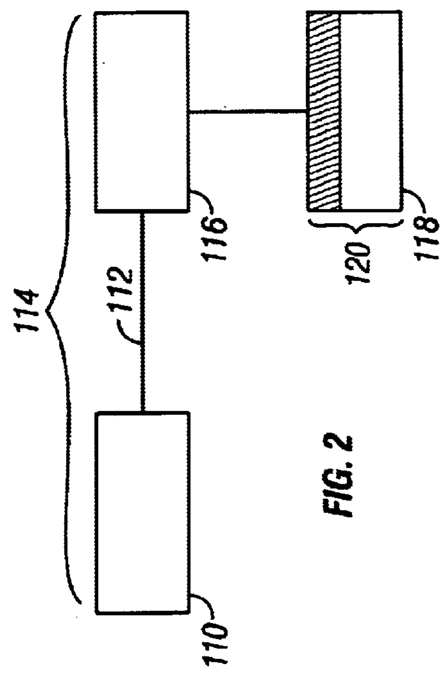
FIG. 2 is a block diagram illustrating one embodiment of a micro-machining apparatus of the present invention that includes the FIG. 1 laser system.

Referring now to FIG. 2, one embodiment of the present invention is a micro-machining apparatus 114 that includes laser system 110 and an output beam directing apparatus 116. Directing apparatus 116 directs output beam 112 to a polymeric surface 118 of an article 120. At least a portion of the polymeric material is micro-machined by output beam 112. Micro-machining can include cutting or scribing of a groove in polymeric surface 118. In various embodiments, polymeric surface 118 can be made of a material selected from polyimide film, FR4 resin, polycarbonate, polypropylene, polyester, teflon, and the like.

In various embodiments, apparatus 114 can be configured to provide a scribing in the polymeric material at a, (i) scan speed in the range of 40 to 2000 mm/s, (ii) width of 5 to 15 microns, and (iii) depth of 2 to 20 microns. In another embodiment, apparatus 114 can be configured to cut the polymeric material at a scan speed in the range of 40 to 2000 mm/s.

In various embodiments, output beam 112 can,. (i) have a power of 1 watts or greater, (ii) be pulsed at 4–15 picoseconds, (iii) have a repetition rate of 80–120 MHz, and the like.

In one method embodiment of the present invention, apparatus 114 produces a UV output beam 112 from system 110 that is used to micro-machine at least a portion of polymeric surface 118 of article 120. In another method of the present invention, UV output beam 112 micro-machines the entire article 120 and not just polymeric surface 118. This embodiment is particularly useful when the majority of the entire article 120 is made of a polymeric material. In other embodiments, article 120 includes a substrate that is not micro-machined.

Two diode pumped solid state $TEM_{00}$ 355 nm UV lasers, one mode-locked at 80 MHz repetition rate the second Q-switched at 30 kHz repetition rate manufactured by Spectra-Physics, Mountain View, California, were compared for purposes of micro-machining polymeric materials. The Q-switched laser provided 4 W average power at a repetition rate of 30 kHz and a pulsewidth of 35 ns. After a 10× beam expander and a galvanometer based scan head, both lasers produced about 3.5 W average power on samples. The final focal spot on the sample surfaces were both about 20 μm in diameter. Two types of materials, polyimide film and FR4 resin were used.

EXAMPLE 1

To cut through a 50.8 μm thick polyimide film, the maximum cutting speed obtained using the mode locked laser was 600 mm/s. The maximum speed obtained using the Q-switched laser was 80 mm/s, as shown in Table 1. The mode locked laser was more than seven times as fast as the Q-switched laser.

To cut through a 127 μm thick polyimide film, the maximum cutting speed obtained using the mode locked laser was 45 mm/s while the maximum speed obtained using the Q-switched laser was 25 mm/s. These results are shown in Table 1. The mode locked laser was almost twice as fast as the Q-switched laser.

For the polyimide films of both thickness, the maximum cutting speeds obtained using the mode locked laser were higher than those obtained using the Q-switched laser. With increasing thickness (from 50.8 μm to 127 μm), however, the difference in the maximum cutting speeds obtained by the two lasers became smaller.

TABLE 1

| Polyimide thickness (μm) | Maximum cutting speed by the mode locked laser (mm/s) | Maximum cutting speed by the Q-switched laser |
|---|---|---|
| 50.8 | 600 | 80 |
| 127.0 | 45 | 25 |

EXAMPLE 2

A number of 20 mm long lines/grooves were scribed on the FR4 surface using both the mode locked and Q-switched lasers at various scanning speeds. The results are shown in Table 2.

To obtain the same groove depth (20 μm), the maximum scanning speed for the mode locked laser was 1000 mm/s, and 100 mm/s for the Q-switched laser. In this embodiment, the mode locked laser provided higher processing speed for purposes of producing the deepest groove. With a 1000 mm/s scanning speed and a pulsewidth of 10 ps, the mode locked laser produced less thermal damage to the material than the Q-switched laser did at 100 mm/s. At the same scanning speed (500 mm/s), the mode locked laser produced a groove depth of 20 μm, and the Q-switched laser produced a groove depth of 5 μm. At 1000 mm/s, the Q-switched laser did not produce a continuous groove because pulses were not overlapping at 30 kHz at this scanning speed. The mode locked laser produced a continuous groove at a very high scanning speed due to its high pulse repetition rate of 80 MHz.

TABLE 2

| Laser | Scanning speed (mm/s) | Groove width* (μm) | Groove depth** (μm) |
|---|---|---|---|
| mode locked laser | 500 | 15 | 20 |
| | 1000 | 12 | 20 |
| | 2000 | 8 | 10 |
| Q-switched laser | 100 | 30 | 20 |
| | 200 | 20 | 18 |
| | 500 | 10 | 5 |
| | 1000 | N/A | N/A |

In Table 2, groove width was measured under microscope at the top of the grooves, and groove depth was roughly estimated under microscope by focusing at the top of grooves and then at the bottom The foregoing of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. A micro-machining apparatus, comprising:

a mode-locked, quasi-cw, infrared laser system including a high reflector and an output coupler defining an oscillator cavity that produces an output beam, a gain medium and a mode locking device positioned in the oscillator cavity and a diode pump source producing a pump beam incident on the gain medium, the infrared laser system being quasi-cw to provide a delivery of pulses that is of a sufficiently high repetition rate to create a continuous cut or scribe;

a second harmonic generator coupled to the oscillator cavity;

a third harmonic generator coupled to the second harmonic generator that produces a UV output beam;

an output beam directing apparatus that directs the output beam to a polymeric surface of an article to create the continuous cut or scribe, wherein at least a portion of the polymeric material is micro-machined by the output beam.

2. The system of claim 1, wherein the gain medium is $Nd:YVO_4$, Nd:YAG, Nd:YLF, Nd:Glass, Ti:sapphire, Cr:YAG, Cr:Forsterite, Yb:YAG, Yb:KGW, Yb:KYW and Yb:glass.

3. The system of claim 1, wherein the polymeric surface is made of a material selected from polyimide film, fiberglass-web-reinforced epoxide resin film, polycarbonate, polypropylene, polyester and polytetrafluoroethylene.

4. The system of claim 1, wherein the system is configured to provide a scribing in the polymeric material at a scan speed in the range of 40 to 2000 mm/s.

5. The system of claim 1, wherein the system is configured to provide a scribing in the polymeric material at a width of 5 to 15 microns.

6. The system of claim 1, wherein the system is configured to provide a scribing in the polymeric material at a depth of 2 to 20 microns.

7. The system of claim 1, wherein the system is configured to a cutting of the polymeric material at a scan speed in the range of 40 to 2000 mm/s.

8. The system of claim 1, wherein the gain medium is Nd:$YVO_4$, Nd:YAG, Nd:YLF, Nd:Glass, Ti:sapphire, Cr:YAG, Cr:Forsterite, Yb:YAG, Yb:KGW, Yb:KYW and Yb:glass.

9. The system of claim 1, wherein the gain medium is Nd:$YVO_4$.

10. (original) The system of claim 9, wherein the Nd:YVO4 gain medium has a doping level of less than 0.5%.

11. The system of claim 9, wherein the Nd:YVO4 gain medium has a doping level of less than 0.5%.

12. The system of claim 1, wherein the mode locking device is a multiple quantum well saturable absorber.

13. The system of claim 1, wherein the mode locking device is a non-linear mirror mode locker.

14. The system of claim 1, wherein the mode locking device is a polarization coupled mode locker.

15. The system of claim 1, wherein the mode locking device is an acousto-optic modulator.

16. The system of claim 1, wherein the output beam has a power of 1 watts or greater.

17. The system of claim 1, wherein the output beam is pulsed at 4–15 picoseconds.

18. The system of claim 17, wherein the output beam has a repetition rate of 80–120 MHz.

19. (original) The system of claim 1, wherein the second harmonic generator is made of LBO.

20. The system of claim 1, wherein the third harmonic generator is made of type II LBO.

21. The system of claim 1, further comprising:

a fourth harmonic generator coupled to the second harmonic generator.

22. The system of claim 21, wherein the fourth harmonic generator is made of type I BBO.

23. The system of claim 1, wherein the diode pump source is fiber coupled.

24. The system of claim 1, wherein the gain medium is Nd:$YVO_4$.

25. A micro-machining apparatus, comprising:

a mode-locked, quasi-cw, infrared laser system including a high reflector and an output coupler defining an oscillator cavity that produces an output beam, a gain medium and a mode locking device positioned in the oscillator cavity and a diode pump source producing a pump beam incident on the gain medium and a first amplifier, the infrared laser system being quasi-cw to provide a delivery of pulses that is of a sufficiently high repetition rate to create a continuous cut or scribe;

a second harmonic generator coupled to the oscillator cavity;

a third harmonic generator coupled to the second harmonic generator that produces a UV output beam; and an output beam directing apparatus that directs the output beam to a polymeric surface of an article to create the continuous cut or scribe, wherein at least a portion of the polymeric material is micro-machined by the output beam.

26. The system of claim 25, wherein the system is configured to provide a scribing in the polymeric material at a scan speed in the range of 40 to 2000 mm/s.

27. The system of claim 25, wherein the system is configured to provide a scribing in the polymeric material at a width of 5 to 15 microns.

28. The system of claim 25, wherein the system is configured to provide a scribing in the polymeric material at a depth of 2 to 20 microns.

29. The system of claim 25, wherein the system is configured to a cutting of the polymeric material at a scan speed in the range of 40 to 2000 mm/s.

30. The system of claim 25, wherein the polymeric surface is made of a material selected from polyimide film, fiberglass-web-reinforced epoxide resin film, polycarbonate, polypropylene, polyester and polytetrafluoroethylene.

31. A method of micro-machining a polymeric surface of an article, comprising:

providing a mode-locked, quasi-cw, infrared laser system including a high reflector and an output coupler defining an oscillator cavity that produces an output beam, a gain medium and a mode locking device positioned in the oscillator cavity, the infrared laser system being quasi-cw to provide a delivery of pulses that is of a sufficiently high repetition rate to create a continuous cut or scribe;

producing a quasi-cw UV output beam and provide a delivery of pulses that is sufficient to create a continuous cut or scribe in an article;

using the UV output beam to micro-machine at least a portion of a polymeric surface of the article to create the continuous cut or scribe.

32. The method of claim 31, wherein micro-machining includes cutting or scribing of a groove.

33. The method of claim 32, wherein the UV output beam scribes the polymeric material at a scan speed in the range of 40 to 2000 mm/s.

34. The method of claim 32, wherein the UV output beam scribes the polymeric material at a width of 5 to 15 microns.

35. The method of claim 32, wherein UV output beam scribes the polymeric material at a depth of 2 to 20 microns.

36. The method of claim 32, wherein the UV output beam cuts the polymeric material at a scan speed in the range of 40 to 2000 mm/s.

37. The method of claim 32, wherein the polymeric surface is made of a material selected from polyimide film, fiberglass-web-reinforced epoxide resin film, polycarbonate, polypropylene, polyester and polytetrafluoroethylene.

38. The method o claim 32, wherein the UV output beam has a power of 1 watts or greater.

39. The method of claim 38, wherein the UV output beam is pulsed at 4–15 picoseconds.

40. The system of claim 39, wherein the UV output beam has a repetition rate of 80–120 MHz.

* * * * *